United States Patent [19]

Ishiguro et al.

[11] Patent Number: 4,697,165
[45] Date of Patent: Sep. 29, 1987

[54] CERAMIC HEATER AND A METHOD OF MANUFACTURING THE SAME

[75] Inventors: Fujio Ishiguro, Nagoya; Hideo Maeda, Kani, both of Japan

[73] Assignee: NGK Insulators, Ltd., Japan

[21] Appl. No.: 790,539

[22] Filed: Oct. 23, 1985

[30] Foreign Application Priority Data

Nov. 1, 1984 [JP] Japan ............................ 59-228874

[51] Int. Cl.⁴ .............................................. H01C 7/00
[52] U.S. Cl. ..................................... 338/34; 338/307; 338/306; 73/27 R; 73/25; 219/538; 219/541; 219/543; 29/611
[58] Field of Search ................. 338/34, 306, 307, 308, 338/309; 73/27 R, 26, 25; 29/611, 620; 422/98; 219/532, 541, 543, 534, 546, 548, 552, 538

[56] References Cited

U.S. PATENT DOCUMENTS 3,061,911 11/1962 Baker .............................. 338/307 X
3,679,473 7/1972 Blatchford et al. ............. 219/543 X
3,989,614 11/1976 Tien .................................. 338/34 X
4,138,812 2/1979 Isenberg .......................... 338/34 X
4,453,397 6/1984 Ohta et al. ....................... 338/34 X Primary Examiner—E. A. Goldberg
Assistant Examiner—M. M. Lateef
Attorney, Agent, or Firm—Parkhurst & Oliff

[57] ABSTRACT

The cermaic heater includes an elongated plate-like ceramic substrate, a resistance heating element arranged on the ceramic substrate and a pair of conductive lead members extending from the resistance heating element and having a specific resistance smaller than that of the resistance heating element. The oxygen sensor element includes a heater unit and a sensor unit, wherein the heater unit has an elongated plate-like ceramic substrate and a resistance heating element and a pair of conductive lead members arranged thereon, and the sensor unit is integrally united with the heater unit and includes an oxygen ion-conducting solid electrolyte body and reference and measuring electrodes and conductive lead members formed thereon.

14 Claims, 12 Drawing Figures

FIG_2d

FIG_2e

FIG_2f

FIG_2g

CERAMIC HEATER AND A METHOD OF MANUFACTURING THE SAME

BACKGROUND OF THE INVENTION

1. Field of the Invention

This invention relates to a ceramic heater which is utilized as a heater by itself or as a heater unit for heating an oxygen sensor by arranging a resistance heating element on an end portion of an elongated plate-like ceramic substrate, and more particularly to an improvement of a lead portion for supplying power to the ceramic heater.

2. Related Art Statement

Heretofore, ceramic heaters obtained by arranging a resistance heating element on an end portion of an elongated rod-like or plate-like ceramic substrate have weidely been used as an insertion type heater or a heater unit for heating an oxygen sensor.

Particularly, there are oxygen sensors used for detecting an oxygen concentration in an exhaust gas of an automotive vehicle, wherein the ceramic heater obtained by arranging the resistance heating element on the end portion of the elongated plate-like ceramic substrate is united with a detecting element so as to heat a detecting portion.

Figure 5:
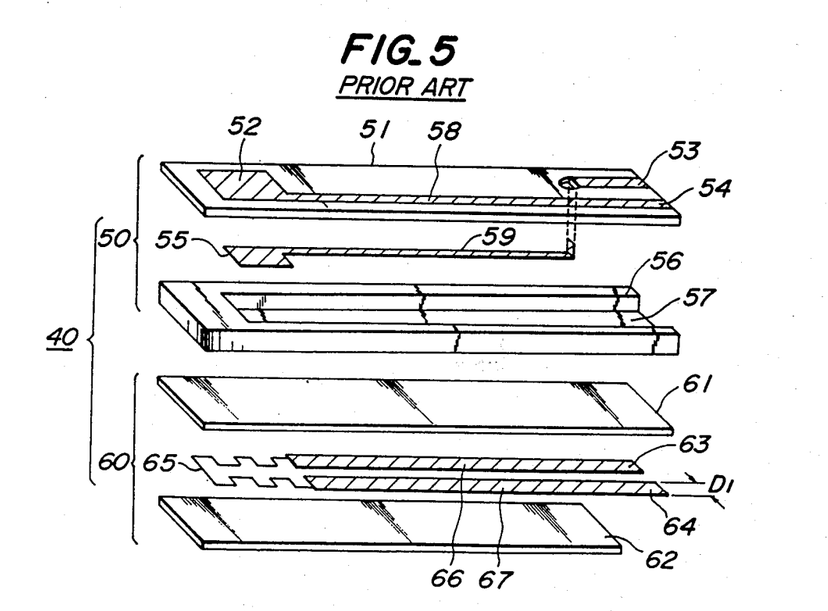
FIG. 5 is an exploded perspective view of the conventional oxygen sensor element.
Figure 6:
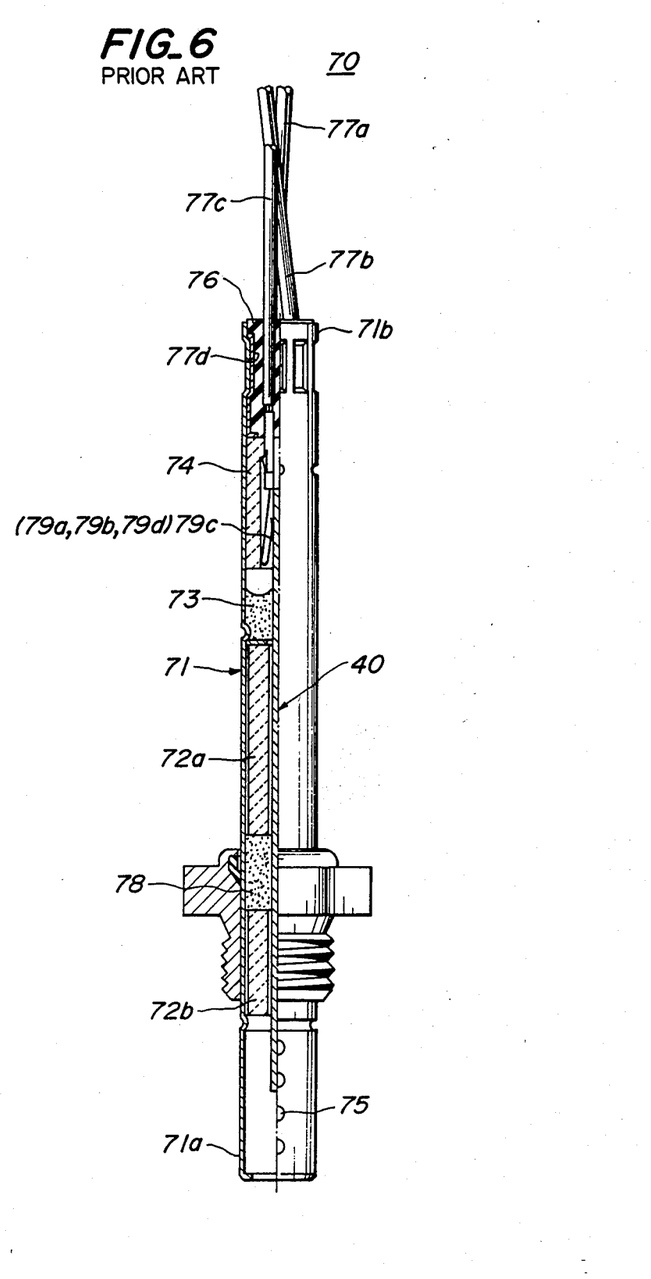
FIG. 6 is a side elevational view partly shown in section of an oxygen sensor as a whole.

Such an oxygen sensor has a structure as shown, for example, in FIGS. 5 and 6.

In FIG. 5 is shown an exploded view of an oxygen sensor element 40. This element 40 generally comprises a sensor unit 50 and a heater unit 60.

In the sensor unit 50, an outer shell is formed by stacking an elongated plate-like solid electrolyte body 51, which is made from an oxygen ion-conducting solid electrolyte consisting mainly of zirconia, on a solid electrolyte plate 56 made from the same material and provided with a groove 57 extending longitudinally from one end of the plate up to the neighborhood of the other end thereof.

To one end of the front surface of the solid electrolyte body 51 is applied to porous measuring electrode 52 made from platinum or the like by printing, while a reference electrode 55 made from the same material is applied to the rear surface of the solid electrolyte body 51 so as to be oppositely located from the measuring electrode 52.

Two lead members 58, 59 each made from the same material as the electrodes 52, 55 are applied in the form of a strip to both surfaces of the solid electrolyte body 51 so a to longitudinally extend from the electrodes 52, 55 to the other end of the body 51, whereby the end portions of these lead members are a reference electrode terminal 53 and a measuring electrode terminal 54, respectively.

In the heater unit 60, two elongated plate-like insulative ceramic bodies 61, 62 are stacked one upon the other, and a resistance heating element 65 is interposed therebetween at their one end portion. Further, two strip-like conductive lead members 66, 67 are interposed between the insulative ceramic bodies 61 and 62 so as to longitudinally extend from both poles of the resistance heating element 65 to the other end of the insulative ceramic bodies 61, 62.

Since the length of the insulative ceramic body 62 is shorter than that of the insulative ceramic body 61, the end portions of the lead members 66 and 67 are exposed from the insulative ceramic body 62 to form connection terminals 63, 64 for connecting to an external power source.

The heater unit 60 is secured to one side of the sensor unit 50 to form an oxygen sensor element 50 provided with a heater.

As shown in FIG. 6, the middle portion of the oxygen sensor element 40 is placed into a longitudinal square hole (not shown) formed in a center of a porcelain insulator 72a and the neighborhood of the detecting portion thereof, thereby exposing it to a gas to be detected such as an exhaust gas or the like, is put into a longitudinal square hole (not shown) formed in a center of a porcelain insulator 72b, which is housed in a hollow protective tube 71 made of a metal. The oxygen sensor element 40 is settled by a filler 73 such as cement, talc, glass or the like and a filler 78 such as talc or the like, which are filled in the upper and lower side of the porcelain insulator 72a.

In the front end portion 71a of the protective tube 71 are formed a plurality of openings 75, whereby the measuring electrode 52, which is located at the end portion of the oxygen sensor element 40 at the front end portion 71a, is contacted with the exhaust gas. Into a back end portion 71b of the protective tube 71 is placed a rubber stopper 76. Lead wires 77a–77c passing through the rubber stopper 76 and a ground wire 77d connected to the protective tube 71 are connected to respective spring pawl members 79a–79d disposed in a porcelain connector 74. Each of these pawl members is electrically contacted with each of the conenction terminals 63, 64 of the heater unit 60, the reference electrode terminal 53 and the measuring electrode terminal 54 provided on the oxygen sensor element 40.

For instance, the oxygen sensor 70 of the above structure is used to detect an oxygen concentration in an exhaust gas by inserting the front end portion 71a of the protective tube 71 into an exhaust pipe of an automotive vehicle. In this case, the resistance heating element 65 in the heater unit 60 is energized to heat the region of the sensor unit 50 including the electrodes 52 and 55 so as to activate the sensor unit 50, whereby the detection accuracy and response of the sensor can be enhanced particularly when the temperature of the exhaust gas is as low as not more than 500° C.

However, when the exhuast gas temperature is as high as about 900° C., the temperature of the front end portion 71a becomes higher and hence the temperature of the connector portion is fairly high due to thermal conduction along the length of the unit and consequently there may be degradation of the terminal wires and the like. For this reason, the use of the elongated type oxygen sensor 70, as described above, becomes advantageous from a viewpoint that the electrically conductive reliability is enhanced by the protection of the lead wires 77a–77d and spring pawl members 79a–79d.

In such an elongated type oxygen sensor, since the length of the lead members 66, 67 becomes long, the resistance of each of these lead members 66, 67 becomes large and consequently the amount of power consumed by the lead members 66, 67 in power supplied to the heater unit including the lead members increases. In order to maintain the detecting portion of the oxygen sensor element above a given temperature, therefore, large power is required as compared with the case of using the sensor element provided with a short lead member.

When the lead members 66, 67 are made from the same material as the resistance heating element 65 in the above oxygen sensor 70, there is adopted a method wherein the width $D_1$ of each of the lead members 66, 67 is widened to reduce the resistance of the lead member 66, 67 in order to decrease the power consumption of these lead members.

However, if it is intended to widen the width of the lead member 66, 67, when firing the assembled oxygen sensor element 40, the problems, as mentioned below, result. That is, when the resistance heating element 65 and the lead members 66, 67 are interposed between the two unfired insulative ceramic layers 61 and 62 and then fired at a state of adhering to the unfired sensor unit 50, since a ratio of total area of the lead members 66, 67 to area of the upper and lower insulative ceramic layers 61, 62 is large, the direct contact or joining area between the upper and lower insulative ceramic layers 61 and 62 becomes small and consequently the joint strength after the firing is lowered (i.e. the bonding force in the region containing the lead members 66, 67 is weak after the firing). Further, since there is usually a difference in the firing shrinkage between the lead member 66, 67 and the insulative ceramic layer 61, 62, the ceramic layers become warped after the firing, so that some cracking between the lead member and the ceramic layer or the peeling of the lead member or the creamic layer may result.

Moreover, since a noble metal such as platinum or the like is used as a component for the lead members 66 and 67, when the width of the lead member 66, 67 is widened, the amount of platinum used becomes large, resulting in the increase of the cost.

The aforementioned problems also occur even when using the heater unit having a long lead member as a heater itself in addition to the above elongated type oxygen sensor.

SUMMARY OF THE INVENTION

It is an object of the invention to provide a ceramic heater which solves the above problems and a method of manufacturing the same.

According to a first aspect of the invention, there is the provision of a ceramic heater comprising an elongated plate-like ceramic substrate, a resistance heating element arranged in the vicinity of at least an end portion of the ceramic substrate and a pair of elongated strip-like conductive lead members extending from the resistance heating element toward the other end of the ceramic substrate, a specific resistance of the conductive lead member being made smaller than that of the resistance heating element.

According to a second aspect of the invention, there is the provision of a method of manufacturing a ceramic heater, comprising the steps of:
(a) print-applying onto an end portion of a surface of an elongated plate-like unfired ceramic substrate a conductive paste for forming a resistance heating element with a given resistance value after the firing;
(b) print-applying onto the surface of the unfired ceramic substrate a conductive paste for forming a conductive lead member with a specific resistance smaller than that of the resistance heating element after the firing so as to extend from the conductive paste forming the resistance heating element toward the other end of the unfired ceramic substrate in the form of a strip; and
(c) firing the entire assembly.

As mentioned above, since the specific resistance of the conductive lead member is smaller than that of the resistance heating element, the power consumption in the conductive lead member can be decreased as compared with the case of using the conductive lead member with a specific resistance equal to that of the resistance heating element. Furthermore, the width of the conductive lead member may also be made narrow.

Since the conductive lead member and the resistance heating element are formed by print-applying the conductive past onto the unfired ceramic substrate and then firing it as previously mentioned, the joint force of the heater as a whole can be enhanced and also the adjustment of specific resistance can easily be performed.

DESCRIPTION OF THE PREFERRED EMBODIMENTS

Figure 1:
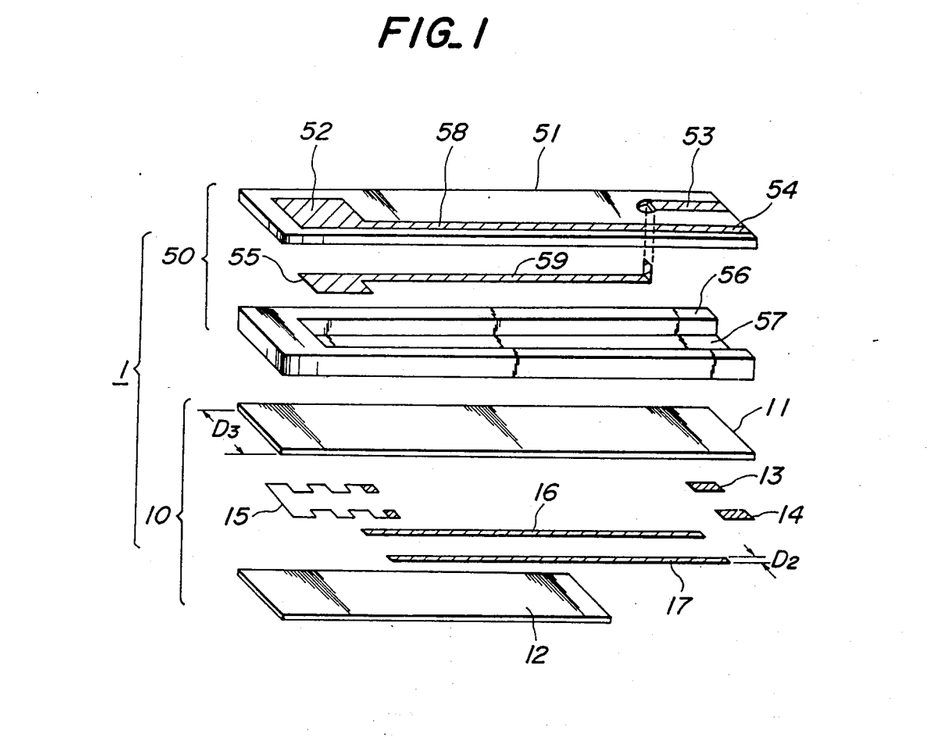
FIG. 1 is an exploded perspective view of a first embodiment of the oxygen sensor element including the heater unit according to the invention.

As a first embodiment of the ceramic heater according to the invention, FIG. 1 shows the application of the ceramic heater to a heater unit of an oxygen sensor element for use in the aforementioned elongated type oxygen sensor, wherein there is explodedly shown an oxygen sensor element 1 housed in the same protective tube 71 as in FIG. 6.

The oxygen sensor element 1 roughly comprises a sensor unit 50 and a heater unit 10, similar to the oxygen sensor element 40 shown in FIG. 5. This sensor unit 50 is the same as in FIG. 5, so that a detailed explanation thereof is omitted here.

The heater unit 10 has a structure substantially similar to that of the heater unit 60 shown in FIG. 5. That is, two elongated plate-like insulative ceramic layers 11 and 12 are stacked one upon the other, and a resistance heating element 15 is interposed therebetween at their one end portions. On the lower surface of the other end portion of the upper insulative ceramic layer 11 are disposed two connection terminals 13 and 14 for connecting to an external power source. Further, two strip-like conductive lead members 16, 17 connecting the connection terminals 13, 14 to both poles of the resistance heating element 15 are sandwiched between the insulative ceramic layers 11 and 12. In this case, since the length of the lower insulative ceramic layer 12 is shorter than that of the upper layer 11, the connection terminals 13, 14 and a portion of each of the lead members 16, 17 are exposed to the atmosphere. Moreover, the ends of the lead members 16, 17 may be extended to the other end of the ceramic layer 11 to be used as the connection terminals 13, 14 in addition to the above illustrated embodiment. In any case, the width of the connection terminal 13, 14 is sufficient to ensure electrical conduction to the outside and is not always coincident with the width $D_2$ of the lead member 16, 17.

The heater unit 10 is united with the sensor unit 50 to form an elongated plate-like ceramic sheet. In other words, the resistance heating element 15 and the lead members 16, 17 are embedded in the ceramic sheet of the above structure.

In the first embodiment of the invention, the specific resistance of the lead member 16, 17 is smaller than that of the resistance heating element 15, and the width $D_2$ of the lead member 16, 17 is narrower than the width $D_1$ of the lead member 66, 67 shown in FIG. 5 (however, the width $D_3$ of the insulative ceramic layer 11, 12 is equal to the width of the insulative ceramic layer 61, 62 shown in FIG. 5).

To be more concrete, the width $D_2$ of the lead member 16, 17 is not more than $\frac{1}{4}$ of the width $D_3$ of the insulative ceramic layer 11, 12, and the total width of the lead members 16 and 17 is not more than $\frac{1}{2}$ of the width $D_3$ of the insulative ceramic layer 11, 12.

If it is intended to use the above oxygen sensor element 1 for detecting an oxygen concentration of an exhaust gas in an automotive vehicle, the size of the ceramic layer is suitable to have a length of about 50–80 mm and a width of about 4–7 mm. When the length is shorter than the above value, heat generated at the side of the resistance heating element 15 and heat radiated from the exhaust gas are mainly transmitted to the connection terminals 13, 14, and consequently there is a possibility of excessively heating the lead wires 77a–77d and spring pawl members 79a–79d as shown in FIG. 6.

Further, since the thickness of the insulative ceramic layer 11, 12 is as thin as about 20–50 μm because this layer is formed by printing, the width $D_2$ of the lead member 16, 17 is preferable to be not more than 1.5 mm. Particularly, when the metal content in the lead member 16, 17 is not less than 80% by volume, the width $D_2$ is preferably not more than 1 mm. This is required to prevent the occurrence of cracking in the insulative ceramic layer 11, 12 at a position of the lead members 16, 17 due to the weak bonding force between the lead member 16, 17 and the insulative ceramic layer 11, 12 and the difference in shrinkage which occurs during firing.

The feature that the resistance heating element 15 and the lead members 16 and 17 are interposed between the two insulative ceramic layers 11 and 12 (i.e. they are embedded in the laminate of the insulative ceramic layers 11, 12) is advantageous for reducing the degradation of the element 15 and members 16, 17 due to heat generation to prolong their service life. Therefore, it is favorable that the insulative ceramic layer is not porous but dense.

Typical materials for the lead members 16, 17 are at least one platinum group metal such as platinum, rhodium, palladium and the like or an alloy or a mixture thereof, to which is added a proper amount of material for adjusting the specific resistance of the lead member. In this case, the amount of material added is controlled so that the lead members 16, 17 may have a maximum electrical conductivity.

Typical materials for the insulative ceramic layes 11, 12 include either zirconia or alumina or both. Additionally, ceramic materials such as mullite, steatite, cordierite, spinel and the like may be used.

As the resistance heating element 15, it is favorable to use a conductor having a positive temperature coefficient of resistance. In this case, for instance, even when a ratio of the resistance value of the resistance heating element 15 to the total resistance value of the lead members 16 and 17 at room temperature is 1:1, if the temperature of the resistance heating element 15 is raised by the application of power, the resistance value of the resistance heating element 15 becomes higher than its value that at room temperature. As a result, such a resistance value of the resistance heating element 15 is higher than the total resistance value of the lead members 16, 17 so that a greater amount of power applied is consumed as a heating energy for the resistance heating element 15, whereby the heating can effectively be performed with a small amount of power.

Since the source voltage is generally constant (12 V in an automotive vehicle), the heat value of the resistance heating element 15 is determined by the current (i.e., amps) value. Thus, if it is possible to decrease the power consumption as described above, the current value may be made small, and the size of lead wire for the power application, contact capacitance between the spring pawl member and the connection terminal 13, 14, may be decreased or at least the reliability may be improved.

From the above facts, it is desirable that the ratio of the resistance value of the resistance heating element 15 to the total resistance values between the connection terminals 13 and 14 is not less than 50%, preferably not less than 70%. This is very effective in the invention.

Next, a concrete embodiment of the manufacture of the aforementioned oxygen sensor element will be described in detail with reference to FIGS. 2a to 2g.

The oxygen sensor element to be manufactured has a length of 50–80 mm and a width of 4–7 mm.

At first, a mixture of 96 mol % of zirconia powder and 4 mol % of yttria powder was weighed to a 1 kg total weight and charged into a polyethylene pot together with a zirconia pebbles grinding media and 2 l of distilled water, which is subjected to a mixing and pulverizing on a pot mill support for 48 hours. Thereafter, the resulting slurry is taken out from the pot and placed in a stainless vessel, which is dried to form a dry cake. Then, the dry cake is calcined in an electric furnace at 1,000° C. for 1 hour under such a state that it is held in an alumina sheath. The resulting calcined body is roughly ground by means of an alumina roll grinder and placed in a polyethylene pot together with the zirconia grinding media and 1.5 wt % of alumina powder as a sintering aid, which is subjected to a dry pulverization on a pot mill support for 48 hours to thereby obtain partly stabilized zirconia powder.

The partly stabilized zirconia powder is mixed with 6 wt % of polyvinyl butyral as a binder and 6 wt % of a plasticizer and thoroughly dispersed into a mixed organic solvent of 50 vol % of diethylene glycol and 50 vol % of butanol. The resulting slurry is shaped into a tape of 0.7 mm in thickness by means of a doctor blade technique.

Figure 2A:
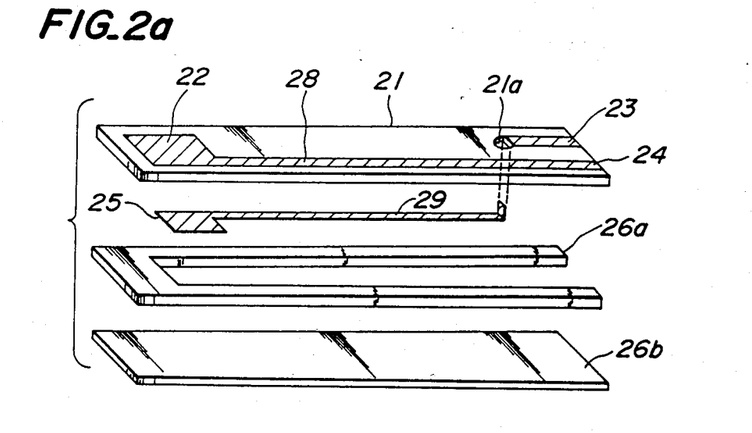
FIGS. 2a to 2g are a flow diagram illustrating steps of manufacturing the oxygen sensor element of FIG. 1, respectively.

This tape is cut at a given size to obtain an unfired body for the solid electrolyte bodies 51, 56 constituting the sensor unit 50 shown in FIG. 1. That is, the unfired body for the solid electrolyte body 51, 56 corresponds to each of three sheets 21, 26a and 26b as shown in FIG. 2a.

On the other hand, 60 vol % of platinum powder is mixed with 40 vol % of the partly stabilized zirconia powder and added with 6 wt % of ethylcellulose as a binder and diethylene glycol as a solvent to prepare a conductive paste. The resulting conductive paste is applied by printing to the upper and lower surfaces of the sheet 21 at a region 25 corresponding to the reference electrode 55, a region 22 corresponding to the measuring electrode 52, regions 28, 29 corresponding to the lead members 58, 59, a region 23 corresponding to the reference electrode terminal 53 and a region 24 corresponding to the measuring electrode terminal 54. Also the conductive paste is applied to an inner periphery of a through-hole 21a.

Figure 2B:
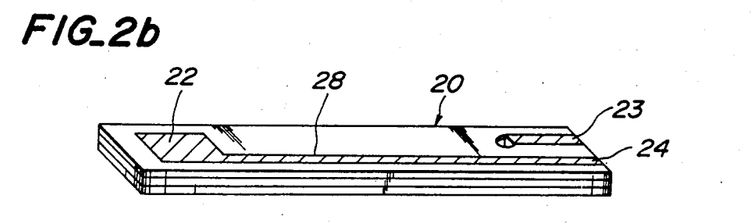

After the applied conductive paste is thoroughly dried, the three solid electrolyte unfired sheets 21, 26a and 26b are laminated one upon another under a pressure to form a laminate 20 as shown in FIG. 2b.

Separately, alumina powder is added with 6 wt % of polyvinyl butyral and diethylene glycol as a solvent to prepare a paste for the formation of an insulative ceramic.

Furthermore, a mixture of 55 vol % of platinum powder and 45 vol % of alumina powder is added with 6 wt % of polyvinyl butyral and diethylene glycol as a solvent to prepare a conductive paste (specific resistance: $20 \times 10^{-5}$ $\Omega$cm) for the formation of the resistance heating element.

In addition, a mixture of 85 vol % of platinum powder and 15 vol % of alumina powder is added with 6 wt % of polyvinyl butyral and diethylene glycol as a solvent to prepare a conductive paste (specific resistance: $2 \times 10^{-5}$ $\Omega$cm) for the formation of the lead member and connection terminal.

Figure 2C:
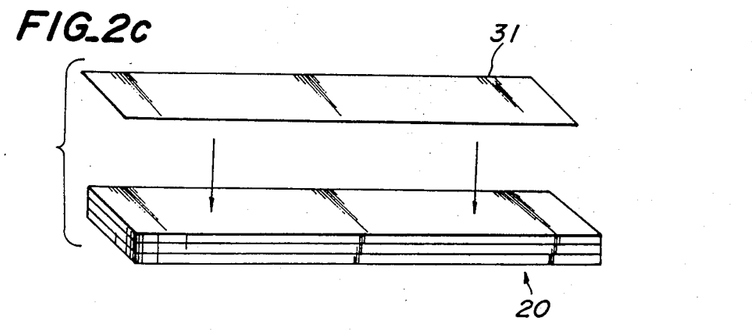

The paste for the formation for the insulative ceramic is applied by printing to the rear surface of the laminate 20 shown in FIG. 2b to form a thin film layer 31 corresponding to the insulative ceramic layer 11 (FIG. 2c).

Figure 2D:
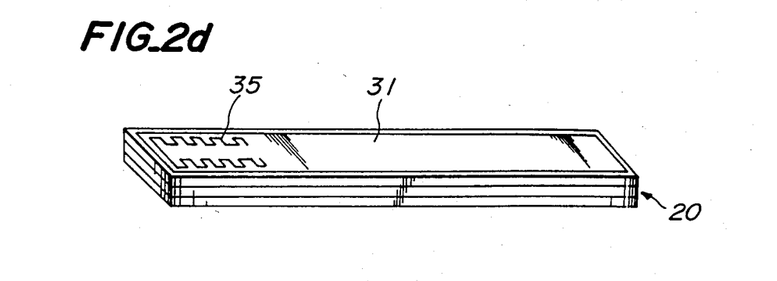

As shown in FIG. 2d, the conductive paste for the formation of the resistance heating element is applied by printing to the surface of the layer 31 at one end portion thereof to form a region 35 corresponding to the resistance heating element 15.

Figure 2E:
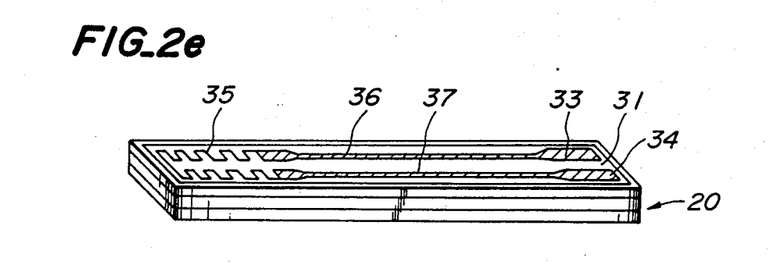

Then, as shown in FIG. 2e, the conductive paste for the formation of lead member and connection terminal is applied by printing to the surface of the layer 31 at the remaining portion thereof to form regions 36 and 37 corresponding to the lead members 16, 17 and regions 33, 34 corresponding to the connection terminals 13, 14, respectively.

Figure 2F:
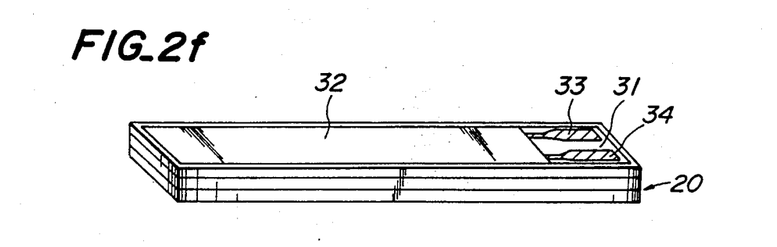

Threafter, as shown in FIG. 2f, the paste for the formation of the insulative ceramic is again applied by printing onto the layer so as to cover the regions 35, 36 and 37 to thereby form a thin film layer 32 corresponding to the insulative ceramic layer 12.

Figure 2G:
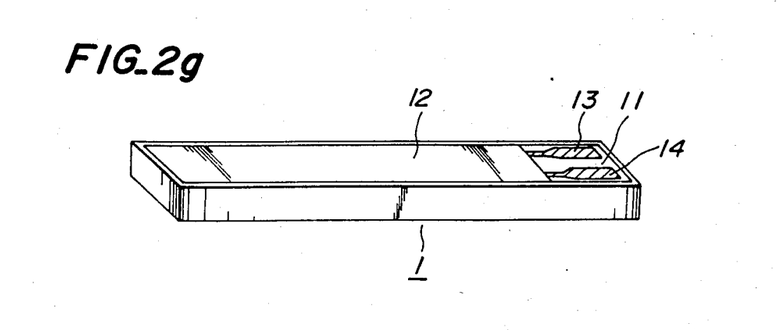

Then, the resulting assembly is placed on a zirconia setter in an electric furnace and fired at 1,450° C. for 6 hours to obtain the oxygen sensor element 1 having the structure shown in FIG. 1 (see FIG. 2g).

In the oxygen sensor element 1 of the above structure, the resistance value between the connection terminals 13 and 14 is about 15 $\Omega$, and the resistance value at room temperature of each of the lead members 16, 17 is about 5 $\Omega$. Further, the oxygen sensor element 1 has a size of about 70 mm in length, about 4.5 mm in width and about 1.6 mm in thickness, wherein the width of each of the lead members 16, 17 is about 0.4 mm.

Moreover, in the oxygen sensor element 1, the warping is not caused after the firing and the joint strength as a whole is sufficiently high. Moreover, the insulative ceramic layer covering the lead members 16 and 17 has a good airtightness without producing gaps or cracks.

Then, an oxygen sensor provided with the above oxygen sensor element 1 (assembled as shown in FIG. 6) is mounted on an exhaust pipe of an automotive vehicle. Thereafter, the vehicle is operated at an air fuel ratio of 13.0, and a direct current of 12 V is applied to the heater unit 10 at the exhaust gas temperature of 300° C. to give a heating power of 4 W to the sensor unit. Under the above conditions, the output of the sensor unit 50 is measured to be a good value of about 900 mV.

For comparison, the oxygen sensor element is manufactured in the same method as described above except that the conductive paste for the formation of the resistance heating element is used for the formation of the regions 36, 37 corresponding to the lead members 16, 17. In this case, warping is caused at the back side at the regions 36, 37, so that the subsequent assembling is difficult. Further, in order to obtain the resistance value of about 5 $\Omega$ in the lead member made from the conductive paste for the formation of the resistance heating element, it is necessary that the width of the lead member is about 1.5 mm. As a result, the total width of the two lead members is 3.0 mm, which becomes larger than a half width of the oxygen sensor element of 4.5 mm.

Moreover, when the assembly having such wide regions for the lead members is fired after a zirconia plate (about 20 g) having the same size as in the oxygen sensor element is put as a weight for preventing the warping, there is not as much warping, but cracking results in the insulative ceramic layer.

Figure 3:
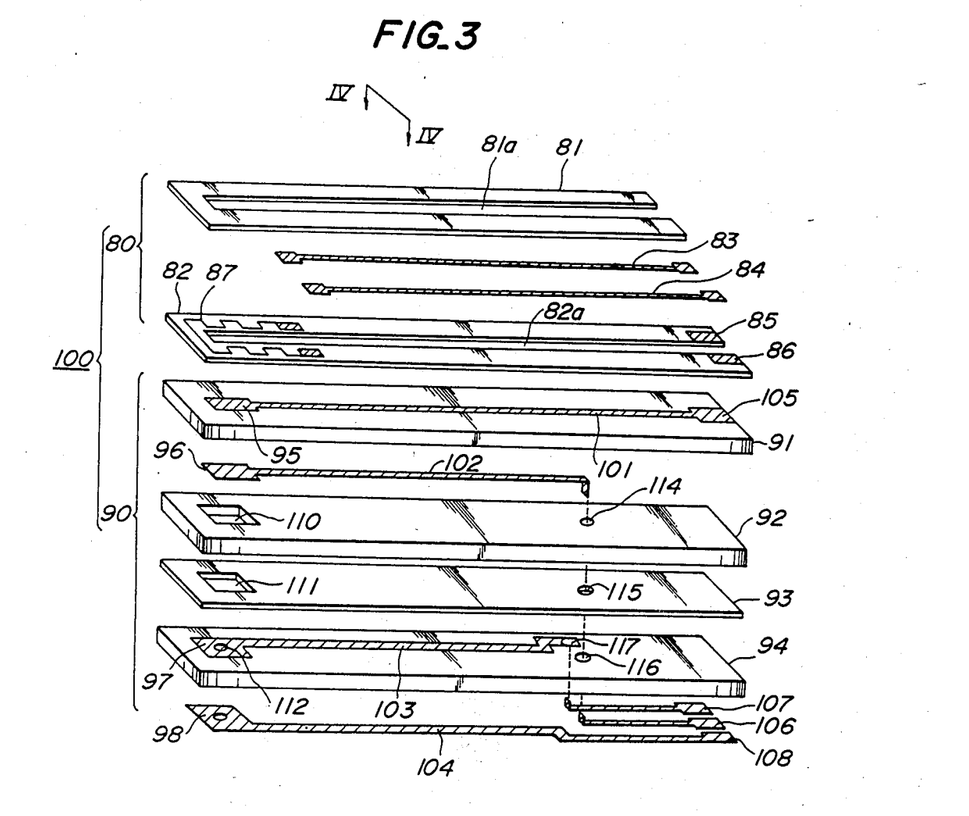
FIG. 3 is an exploded perspective view of a second embodiment of the oxygen sensor element according to the invention.
Figure 4:
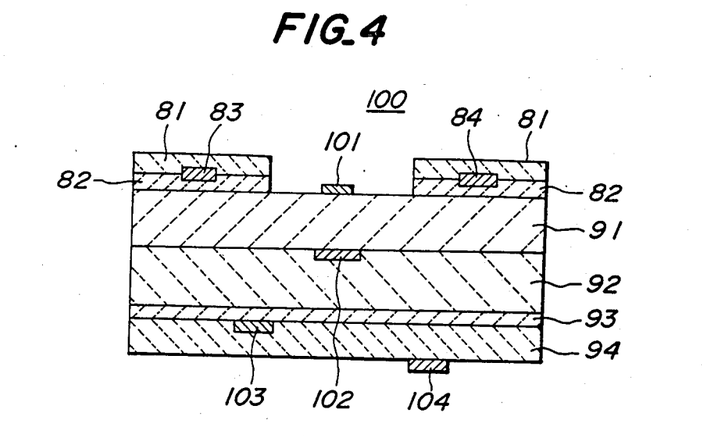
FIG. 4 is a sectional view taken along a line IV—IV of FIG. 3.

Next, the second embodiment of the invention will be described with respect to an elongated type oxygen sensor provided with an oxygen pump. This oxygen sensor is generally used for measuring a partial oxygen pressure in an oxygen rich gas to be tested. FIG. 3 is an exploded view of an oxygen sensor element used in such an oxygen sensor, and FIG. 4 is a sectional view taken along a line IV—IV of FIG. 3.

The oxygen sensor element 100 shown in FIG. 3 generally comprises a sensor unit 90 and a heater unit 80.

In the sensor unit 90, an insulative ceramic layer 93 is interposed between two oxygen ion-conducting solid electrolyte bodies 92 and 94, and further a solid electrolyte body 91 is laminated on the upper surface of the upper solid electrolyte body 92.

On the upper surface of the solid electrolyte body 91 are formed a positive electrode 94 for the oxygen pump at the one end portion and a connection terminal 105 at the other end portion, which are connected to each other through a lead member 101.

Between the solid electrolyte body 91 and the solid electrolyte body 92 are sandwiched a negative electrode 96 for the oxygen pump and a lead member 102, wherein the negative electrode 96 is oppositely located from positive electrode 95 and faces a cavity 110 formed in one end portion of the solid electrolyte body 92.

On the upper surface of the solid electrolyte body 94 are formed a measuring electrode 97 and a lead member 103, while another measuring electrode 98, a lead member 104, a connection terminal 106 connecting to the negative electrode 96 and connection terminals 107, 108 connecting to the respective measuring electrodes 97, 98 are formed on the lower surface of the solid electrolyte body 94.

In the one end portion of the insulative ceramic layer 93 is formed a square window 111 coresponding to the cavity 110, while a diffusion hole 112 communicating with the cavity 110 is formed in the one end portion of the solid electrolyte body 94. Further, a hole corresponding to the diffusion hole 112 is formed in each of the measuring electrodes 97 and 98. In the solid electrolyte bodies 92 and 94 and the insulative ceramic layer 93 are formed through-holes 114, 115, 116 and 117 for guiding the lead members 102 and 103 to the lower surface of the solid electrolyte body 94 (the inner periphery of each of these through-holes is coated with a conductor).

In the sensor unit 90 of the above structure, a gas to be tested is diffused into the cavity 110 through the diffusion hole 112. Then, the partial oxygen pressure of the test gas in the cavity 110 is made to be substantially zero by the action of the oxygen pump (composed of two electrodes 95 and 96 and the solid electrolyte body 91). Under such a condition, an oxygen concentration in the test gas is determined from output voltages of the measuring electrodes 97 and 98 and a pumping current flowing between the electrodes 95 and 96.

In the heater unit 80, a resistance heating element 87 is sandwiched between two insulative ceramic layers 81 and 82 at their one end portion, while two lead members 83 and 84 are extended from both the poles of the resistance heating element 87 toward the other ends of the ceramic layers 81 and 82. Further, connection terminals 85 and 86 connecting to the respective lead members 83 and 84 are formed on the other end portion of the insulative ceramic layer 82. Moreover, since the length of the insulative ceramic layer 82 is somewhat shorter than that of the insulative ceramic layer 82, the connection terminals 85 and 86 are at the exposed state.

Further, slits 81a and 82a for exposing the electrode 95 and the lead member 101 to the atmosphere are formed in the middle portions of the insulative ceramic layers 81 and 82 along their longitudinal direction, respectively.

The specific resistance of the lead member 83, 84 is smaller than that of the resistance heating element 87, and the width of the lead member 83, 84 is narrower than that of the lead member 66, 67 shown in FIG. 5.

In the manufacture of the heater unit 80, a mixture of 75 vol % of platinum powder and 25 vol % of alumina powder (specific resistance: $10 \times 10^{-5}$ Ω.cm) is used as a conductive paste for the formation of the resistance heating elment 87, while a mixture of 90 vol % of platinum powder and 10 vol % of alumina powder (specific resistance: $1.5 \times 10^{-5}$ Ω.cm) is used as a conductive paste for the formation of the lead members 83 and 84.

When the oxygen sensor element 100 has, for example, a size of 60 mm in length and 6 mm in width, the width of the lead member 83, 84 is adjusted to be about 1.0 mm after the firing.

Thus, the resistance between the connection terminals 85 and 86 is 5.0 Ω, and the total resistance of the lead members 83 and 84 is 1.4 Ω.

Further, the width of each of the lead members 101 and 102 for the electrodes 95 and 96 is made wider (e.g. 0.7 mm) so as to suppress the reduction of the pumping voltage due to the resistance of the lead member as far as possible, while the width of each of the lead members 103 and 104 for the measuring electrodes 97 and 98 is 0.5 mm.

When the width of each lead member is selected as mentioned above, there is no occurrence of warping and cracking after firing.

FIG. 4 shows a sectional view of the oxygen sensor element taken along line IV—IV of FIG. 3, from which it is understood that the lead members 83 and 84 in the heater unit 80 and the lead member 101 for the positive electrode of the oxygen pump in the sensor unit 90 are arranged on the solid electrolyte body 91 side by side in substantially the same plane.

When the total width of the lead members 83 and 84 is more than a half width of the oxygen sensor element 100, if the lead member 101 is further arranged, warping, cracking, peeling and the like of the lead members result during firing of the oxygen sensor element. On the other hand, when the total width of the lead members 83 and 84 is more than ⅔ of the width of the oxygen sensor element, the arrangement of the lead member 101 can not physically be realized. On the contrary, in the illustrated embodiment of FIGS. 3 and 4, the power consumption in the lead members 83 and 84 can be reduced by making the specific resistance of each lead member small as compared with the specific resistance of the resistance heating element, and also the other lead member can be arranged in substantially the same plane in addition to the lead members 83 and 84 by making the width of the lead member 83, 84 narrow. Thereby, the width of each of the ceramic layers 81 and 82 may be made narrow for insulating the lead members to each other. Therefore, it is possible to manufacture an oxygen sensor having a complicated and multifunctional structure in addition to the embodiment of FIGS. 3 and 4.

In the manufacture of the oxygen sensor elements 1 and 100, there may be adopted any methods other than the method shown in FIGS. 2a to 2g, for example, a method of forming connection terminals 13, 14, 85, 86 after the firing and the like.

Although the above illustrated embodiments have been described with respect to the oxygen sensor element provided with the ceramic heater, the invention may be applied to a heater itself, a heater unit for equipment requiring heating other than the oxygen sensor element and the like.

Further, although the greater part of the resistance heating element and the lead members are sandwiched between the insulative ceramic layers in the above illustrated embodiments, they may be arranged on the ceramic layer at an exposed state as a whole. Moreover, the heater unit may be located in the sensor unit.

As mentioned above, according to the invention, the specific resistance of the conductive lead member in the elongated type ceramic heater is made smaller than the specific resistance of the resistance heating element, so that the power consumption in the conductive lead member can be reduced and the heating can efficiently be performed with a small amount of power consumption.

Further, since the width of the conductive lead member may be made narrow to reduce an area of the lead member occupied in the ceramic heater, the joint force between the ceramic layers covering the conductive lead member becomes large, and there is not caused a fear of causing the warping or cracking after the firing.

Moreover, when the conductive paste is applied by printing and then fired to form the conductive lead member and the resistance heating element, the joint force of the ceramic heater as a whole can be enhanced and the adjustment of specific resistance may easily be performed.

What is claimed is:

1. A ceramic heater comprising an elongated plate-like ceramic substrate having a first end portion and a second end portion and a transverse width, a resistance heating element arranged in the vicinity of said first end portion of said ceramic subtrate, said resistance heating element having two electrical connections and a pair of elongated strip-like conductive lead members, each of said lead members extending from one connection of said resistance heating element toward the second end portion of said ceramic substrate; each of said lead members having a specific electrical resistance which is less than a specific electrical resistance of said resistance heating element and each of said lead members having a transverse width, wherein a sum of the transverse widths of the lead members is not more than one half the transverse width of the ceramic substrate.

2. The ceramic heater accoding to claim 1, wherein all of said resistance heating element and at least a portion of said lead members close to said resistance heating element are embedded in said ceramic substrate.

3. The ceramic heater according to claim 1, wherein said ceramic substrate is a substantially rectangular substrate having an elongated length of not more than 50 mm and the transverse width is not more than 7 mm.

4. An oxygen sensor element comprising a heater unit and a sensor unit; said heater unit comprising an elongated plate-like ceramic substrate having a first end portion and a second end portion and a transverse width, a resistance heating element arranged in the vicinity of said first end portion of said ceramic substrate, said resistance heating element having two electrical connections and a pair of elongated strip-like conductive lead members, each of said lead members extending from one connection of said resistance heating element toward the second end portion of said ceramic substrate, each of said conductive lead members having a specific electrical resistance which is less than a specific electrical resistance of said resistance heating element and each of said lead members having a transverse width, wherein a sum of the transverse widths of the lead members is not more than one half the transverse width of the ceramic substrate; said sensor unit comprising an oxygen ion-conducting solid electrolyte body, at least one measuring electrode and one reference electrode arranged in the vicinity of said first end portion of said solid electrolyte body, and conductive lead members extending from each of said measuring and reference electrodes toward said second end portion of said solid electrolyte body; wherein said heater unit is integrally attached to said sensor, thereby heating at least one of said electrode and said reference electrode.

5. The oxygen sensor element according to claim 4, wherein all of said resistance heating element and at least a portion of said lead members close to said resistance heating element in said heater unit are embedded in said ceramic substrate.

6. The oxygen sensor element according to claim 4, wherein at least one strip-like conductive lead member is arranged on said ceramic substrate parallel to and in substantially a same plane as said lead members in said heater unit, and a total transverse width of these lead members is not more than half of the transverse width of said ceramic substrate.

7. The oxygen sensor element according to claim 6, wherein said strip-like conductive lead member is a conductor connecting at least one of said measuring electrode and reference electrode of said sensor unit.

8. The oxygen sensor element according to claim 4, wherein said conductive lead members in said heater and sensor unit comprise a conductive material consisting essentially of a platinum group metal.

9. The oxygen sensor element according to claim 8, wherein said platinum group metal is selected from the group consisting of platinum, rhodium, palladium, and mixtures thereof.

10. The oxygen sensor element according to claim 8, wherein said conductive material contains ceramics.

11. The oxygen sensor element according to claim 10, wherein said ceramics comprises at least one of zirconia and alumina.

12. The oxygen sensor element according to claim 4, wherein said resistance heating element and said conductive lead members each having a given electrical resistance value are formed by print-applying a conductive paste onto said ceramic substrate at regions corresponding to said resistance heating element and conductive lead members and subsequent firing thereof.

13. A method of manufacturing a ceramic heater, comprising the steps of:
(a) print-applying onto a first end portion of a surface of an elongated plate-like unfired ceramic substrate a conductive paste for forming a resistance heating element having a given electrical resistance value after firing thereof and a transverse width;
(b) print-applying onto the surface of said unfired ceramic substrate a conductive paste for forming at least one conductive lead member having a specific electrical resistance which is smaller than the electrical resistance of said resistance heating element after firing thereof so as to extend from said conductive paste forming said resistance heating element toward a second end portion of said unfired ceramic substrate in the form of at least one strip; and said at least one strip having a transverse width, wherein a sum of the transverse widths of said at least one strip is not more than one-half the transverse width of the ceramic substrate, thereby forming an unfired heater; and
(c) firing the unfired heater.

14. The ceramic heater according to claim 13, wherein said ceramic substrate is a substantially rectangular substrate having an elongated length of not more than 50 mm and the transverse width is not more than 7 mm.

* * * * *